(12) United States Patent  (10) Patent No.: US 7,767,218 B2
Bachman et al.  (45) Date of Patent: Aug. 3, 2010

(54) PAIN RELIEF IMPLANT PELLET AND METHOD USING SAME

(76) Inventors: Stephen E. Bachman, 6824 Glenoak La., Amarillo, TX (US) 79109; Michael E. Hubbert, 4401 S. Coulter, Apt. #915, Amarillo, TX (US) 79109

( * ) Notice: Subject to any disclaimer, the term of this patent is extended or adjusted under 35 U.S.C. 154(b) by 1597 days.

(21) Appl. No.: 10/381,864

(22) PCT Filed: Sep. 26, 2001

(86) PCT No.: PCT/US01/42314

§ 371 (c)(1),
(2), (4) Date: Jul. 14, 2003

(87) PCT Pub. No.: WO02/26179

PCT Pub. Date: Apr. 4, 2002

(65) Prior Publication Data

US 2004/0022832 A1  Feb. 5, 2004

(51) Int. Cl.
*A61F 2/02* (2006.01)
(52) U.S. Cl. ..................................... 424/423
(58) Field of Classification Search ................... 424/423
See application file for complete search history.

(56) References Cited

U.S. PATENT DOCUMENTS

| 5,522,797 A | 6/1996 | Grimm | 604/61 |
| 5,874,098 A | 2/1999 | Stevens et al. | 424/408 |
| 5,919,473 A * | 7/1999 | Elkhoury | 424/422 |

FOREIGN PATENT DOCUMENTS

| WO | WO 95/01384 | * 12/1995 |
| WO | WO 99/01114 | * 1/1999 |

* cited by examiner

*Primary Examiner*—Carlos A Azpuru
(74) *Attorney, Agent, or Firm*—Dale F. Regelman; Quarles & Brady LLP (57) ABSTRACT

An emplantable pellet comprising one or more pain relief agents. A method to relief pain at the injection site of one or more implanted pharmaceutical pellets comprising the step of implanting one or more of Applicant's implantable pellets. A method to adjust the in vivo rate of release of one or more pain relief agents from Applicants' implantable pellets. A method to adjust the rate of systemic delivery of one or more pharmaceutical agents implanted adjacent one or more of Applicants' implantable pellets.

1 Claim, 10 Drawing Sheets

| | A | B | C | D | E | F | G | H | I | J | K | L | M | N | O | P | Q | R | S |
|---|---|---|---|---|---|---|---|---|---|---|---|---|---|---|---|---|---|---|---|
| ANESTHETIC AGENT(S) | 95 | 90 | 85 | 80 | 75 | 70 | 65 | 60 | 55 | 50 | 45 | 40 | 35 | 30 | 25 | 20 | 15 | 10 | 5 |
| ANALGESIC AGENT(S) | 5 | 10 | 15 | 20 | 25 | 30 | 35 | 40 | 45 | 50 | 55 | 60 | 65 | 70 | 75 | 80 | 85 | 90 | 95 |

FIG. 5A

| | AA | AB | AC | AD | AE | AF | AG | AH | AI | AJ | AK | AL | AM | AN | AO | AP | AQ | AR | AS |
|---|---|---|---|---|---|---|---|---|---|---|---|---|---|---|---|---|---|---|---|
| ANESTHETIC AGENT(S) | 95 | 90 | 85 | 80 | 95 | 90 | 85 | 80 | 75 | 70 | 65 | 60 | 55 | 50 | 95 | 90 | 85 | 80 | 75 |
| ANTI-INFLAMMATORY | | | | | 5 | 10 | 15 | 20 | 25 | 30 | 35 | 40 | 45 | 50 | | | | | |
| EXCIPIENT | | | | | | | | | | | | | | | 5 | 10 | 15 | 20 | 25 |
| SURFACTANT | 5 | 10 | 15 | 20 | | | | | | | | | | | | | | | |

FIG. 5B

| | AT | AU | AV | AW | AX | AY | AZ | BA | BB | BC | BD | BE | BF | BG | BH | BI | BJ | BK | BL |
|---|---|---|---|---|---|---|---|---|---|---|---|---|---|---|---|---|---|---|---|
| ANESTHETIC AGENT(S) | 70 | 65 | 60 | 55 | 50 | 95 | 90 | 85 | 80 | 80 | 80 | 75 | 75 | 75 | 70 | 70 | 70 | 70 | 70 |
| ANTI-INFLAMMATORY | 30 | 35 | 40 | 45 | 50 | 2 | 4 | 5 | 10 | 5 | 5 | 10 | 10 | 5 | 20 | 5 | 5 | | 15 |
| EXCIPIENT | | | | | | 2 | 4 | 5 | 5 | 10 | 5 | 10 | 5 | 10 | 5 | 20 | 5 | 15 | 15 |
| SURFACTANT | | | | | | 1 | 2 | 5 | 5 | 5 | 10 | 5 | 10 | 10 | 5 | 5 | 20 | 15 | |

FIG. 6A

| | CA | CB | CC | CD | CE | CF | CG | CH | CI | CJ | CK | CL | CM | CN | CO | CP | CQ | CR | CS |
|---|---|---|---|---|---|---|---|---|---|---|---|---|---|---|---|---|---|---|---|
| ANESTHETIC AGENT(S) | 95 | 90 | 85 | 80 | 95 | 90 | 85 | 80 | 75 | 70 | 65 | 60 | 55 | 50 | 95 | 90 | 85 | 80 | 75 |
| ANTI-INFLAMMATORY | | | | | 5 | 10 | 15 | 20 | 25 | 30 | 35 | 40 | 45 | 50 | | | | | |
| EXCIPIENT | | | | | | | | | | | | | | | 5 | 10 | 15 | 20 | 25 |
| SURFACTANT | 5 | 10 | 15 | 20 | | | | | | | | | | | | | | | |

FIG. 6B

| | CT | CU | CV | CW | CX | CY | CZ | DA | DB | DC | DD | DE | DF | DG | DH | DI | DJ | DK | DL |
|---|---|---|---|---|---|---|---|---|---|---|---|---|---|---|---|---|---|---|---|
| ANESTHETIC AGENT(S) | 70 | 65 | 60 | 55 | 50 | 95 | 90 | 85 | 80 | 80 | 80 | 75 | 75 | 75 | 70 | 70 | 70 | 70 | 70 |
| ANTI-INFLAMMATORY | 30 | 35 | 40 | 45 | 50 | 2 | 4 | 5 | 10 | 5 | 5 | 10 | 10 | 5 | 20 | 5 | 5 | | 15 |
| EXCIPIENT | | | | | | 2 | 4 | 5 | 5 | 10 | 5 | 10 | 5 | 10 | 5 | 20 | 5 | 15 | 15 |
| SURFACTANT | | | | | | 1 | 2 | 5 | 5 | 5 | 10 | 5 | 10 | 10 | 5 | 5 | 20 | 15 | |

FIG. 7A

| | EA | EB | EC | ED | EE | EF | EG | EH | EI | EJ | EK | EL | EM | EN | EO | EP | EQ | ER | ES |
|---|---|---|---|---|---|---|---|---|---|---|---|---|---|---|---|---|---|---|---|
| ANESTHETIC AGENT(S) ANALGESIC AGENT(S) COMBINATION | 95 | 90 | 85 | 80 | 95 | 90 | 85 | 80 | 75 | 70 | 65 | 60 | 55 | 50 | 95 | 90 | 85 | 80 | 75 |
| ANTI-INFLAMMATORY | | | | | 5 | 10 | 15 | 20 | 25 | 30 | 35 | 40 | 45 | 50 | | | | | |
| EXCIPIENT | | 10 | 15 | 20 | | | | | | | | | | | 5 | 10 | 15 | 20 | 25 |
| SURFACTANT | 5 | | | | | | | | | | | | | | | | | | |

FIG. 7B

| | ET | EU | EV | EW | EX | EY | EZ | FA | FB | FC | FD | FE | FF | FG | FH | FI | FJ | FK | FL |
|---|---|---|---|---|---|---|---|---|---|---|---|---|---|---|---|---|---|---|---|
| ANESTHETIC AGENT(S) ANALGESIC AGENT(S) COMBINATION | 70 | 65 | 60 | 55 | 50 | 95 | 90 | 85 | 80 | 80 | 80 | 75 | 75 | 75 | 70 | 70 | 70 | 70 | 70 |
| ANTI-INFLAMMATORY | 30 | 35 | 40 | 45 | 50 | 2 | 4 | 5 | 10 | 5 | 5 | 10 | 10 | 5 | 20 | 5 | 5 | | |
| EXCIPIENT | | | | | | 2 | 4 | 5 | 5 | 10 | 5 | 10 | 5 | 10 | 5 | 20 | 5 | 15 | 15 |
| SURFACTANT | | | | | | 1 | 2 | 5 | 5 | 5 | 10 | 5 | 10 | 10 | 5 | 5 | 20 | 15 | |

PAIN RELIEF IMPLANT PELLET AND METHOD USING SAME

FIELD OF THE INVENTION

The present invention is broadly concerned with a pain relief composition in implantable pellet form, and a method to relieve pain using such implantable pellets.

BACKGROUND OF THE INVENTION

Animal well-being and treatment are major concerns for animal welfare groups and animal agriculturalists. Animal well-being and treatment are continual concerns because stressed or uncomfortable animals do not efficiently and profitably produce milk, meat, or eggs.

Implant technology, that is to say, procedures involving subcutaneous implant of pharmaceuticals and medical devices, is now well accepted and widespread in the areas of animal health and production enhancement as well as human health. Growth stimulants are commonly used to enhance the body weight of animals which are raised for harvesting, such as cattle, swine, sheep, turkeys, chickens, and the like.

In the case of cattle and sheep, approved growth stimulants are administered as solid pellets which are injected by an implanter equipped with a hypodermic needle. The needle is used to make a surface self-sealing and, non-coring implant receiving puncture beneath the skin of the ear of the animal. Small pellets of growth-promoting hormones are forced through the needle and left under the skin as the needle is removed from the ear. The ears are commonly discarded in harvesting, such that no unabsorbed residues of such pellets will end up in food products intended for humans or domestic animals. The pharmaceutical in the pellets is normally formulated for timed release and continuous, sustained absorption of the active ingredients over an extended period of time.

Many types of pharmaceuticals such as bioactive compounds may also be implanted and include insulin, endocrine hormones for control of reproduction, vaccines, and biocides for flea and parasite control in humans, horses, and domestic animals such as dogs and cats. The compounds may be administered subcutaneously at any suitable location on the body. Included as such a pharmaceutical are synthetic derivatives of naturally occurring compounds such as trenbolone acetate, a synthetic derivative of testosterone currently used in cattle growth-promoting implants. As those skilled in the art will appreciate, similar therapeutic procedures may be employed to implant drug delivery devices such as controlled release osmotic pumps in humans and animals as well as transponder devices in animals.

In the case of food-producing animals, the pellets are normally implanted while an animal is confined in a chute. An ear is grasped in one hand, and an implanter device having a large hypodermic needle is used to puncture the hide and subcutaneously inject a pellet dose into an implant-receiving puncture. The implanting must be done carefully to insure that the pellets are properly placed and that no pellet remains extending from the puncture outside the hide. The procedure must be carried out quickly since the animals are not entirely cooperative and may shake their heads to free the held ear.

In addition to implanting pharmaceutical pellets, is it also known in the art to implant certain anti-inflammatory agents. As those skilled in the art will appreciate, when tissue injury occurs, whether caused by bacteria, trauma, chemicals, heat, or any other phenomenon, the body's inflammatory response is stimulated. In response to signals released from the damaged cells (e.g., cytokines), extravascularization of immune effector cells is induced. Under ordinary circumstances these invading immune effector cells kill the infectious agent and/or infected or damaged cells (through the release of killing substances such as superoxides, performs, and other antimicrobial agents stored in granules), remove the dead tissues and organisms (through phagocytosis), release various biological response modifiers that promote rapid healing and covering of the wound (quite often resulting in the formation of fibrotic scar tissue), and then, after the area is successfully healed, exit from the site of the initial insult.

Once the site is perceived to be normal, the local release of inflammatory cytokines ceases and the display of adhesion molecules on the vessel endothelium returns to basal levels. In some cases, however, the zeal of these interacting signals and cellular systems, which are designed to capture and contain very rapidly multiplying infectious agents, act to the detriment of the body, killing additional, otherwise healthy, surrounding tissue. This additional unnecessary tissue death further compromises organ function and sometimes results in death of the individual.

The present invention provides a pain relief pellet system which delivers localized, controlled and sustained release of a predetermined quantity of one or more pain relief agents, in optional combination with one or more anti-inflammatory agents, one or more polymeric excipients, and/or one or more surfactants. Applicants' anesthetic/analgesic pellet system can be used in combination with one or more pharmaceutical implants as part of a single procedure in order to provide desired pharmaceutical to the animal while simultaneously alleviating pain and, optionally, inflammation at the injection site.

SUMMARY OF THE INVENTION

The present invention includes an implantable pain relief pellet. Applicants' invention further includes a method for implantation of same. In certain embodiments, Applicants' method also includes implantation of one or more pharmaceutical pellet, thereby providing localized, sustained, anesthetic/analgesic release at an injection site in order to reduce pain around the site of the injection.

In certain embodiments, Applicants' method also includes implantation of one or more anti-inflammatory pellets, thereby providing localized, sustained, anti-inflammatory release at an injection site in order to reduce inflammation around the site of the injection.

Applicants' invention further comprises a pellet system which includes an implanter apparatus for subcutaneously injecting pharmaceutical pellets into an animal through the bore of a hypodermic needle which is remotely coupled to a pellet magazine, and simultaneously implanting one or more anesthetic/analgesic/anti-inflammatory pellet into the injection site. Applicants' invention further includes a method comprising implantation of predetermined doses of one or more pharmaceutical or combination and an anesthetic/analgesic/anti-inflammatory agent(s) in a single injection.

Applicants' invention further comprises a method which permits an operator to selectively implant an anesthetic/analgesic dose into an animal, including humans. Applicants' invention further comprises a method which permits serial injection of large numbers of animals in a single session.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

It is to be understood that the disclosed embodiments are merely exemplary of the invention, which may be embodied in various forms. Therefore, specific structural, composition, and/or functional details disclosed herein are not to be interpreted as limiting, but merely as a basis for the claims and as a representative basis for teaching one skilled in the art to variously employ the present invention in virtually any appropriately detailed structure, composition, and/or method.

Applicants' invention comprises an implantable pellet comprising one or more pain relief agents. By pain relief agent, Applicants mean one or more anesthetic agents and/or one or more analgesic agents. By anesthetic agent, Applicants mean a composition that induces a partial or total loss of the sense of pain, temperature, touch, and the like. By analgesic agent, Applicants mean a composition that induces a state of not being able to feel pain. Applicants' pain relief pellet can be formed by various methods including, but not limited to, compression molding and/or encapsulation.

Figure 5A:
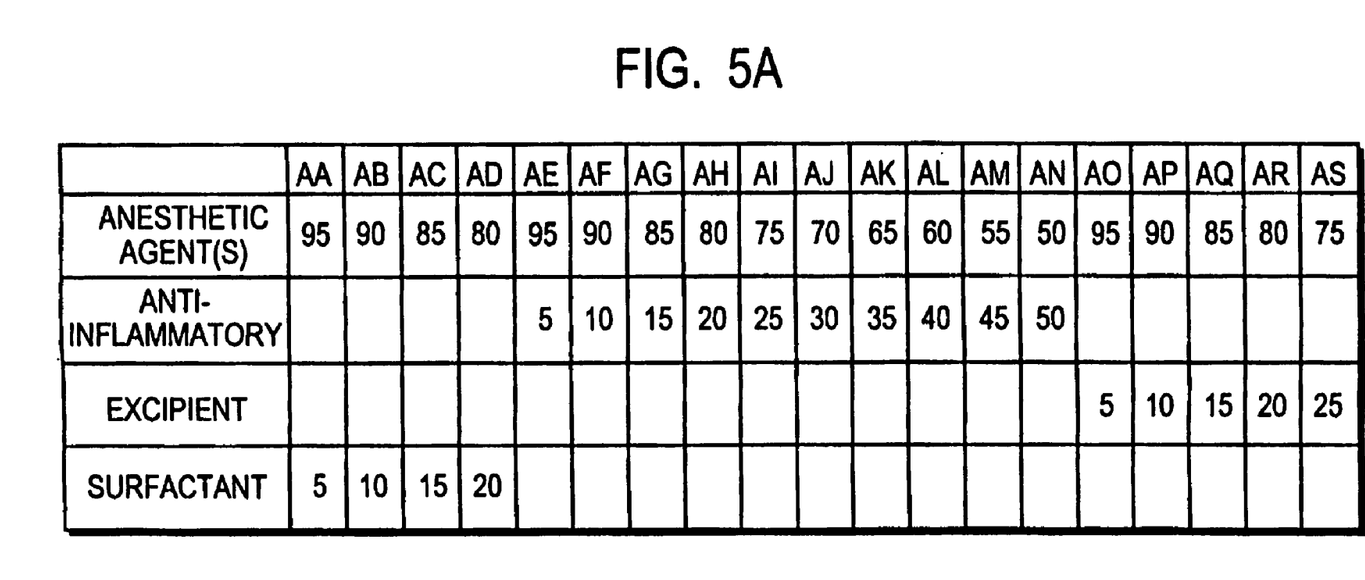
FIG. 5A recites Applicants' formulations AA through AS which include one or more anesthetic agents in combination with one or more additional ingredients.
Figure 5B:
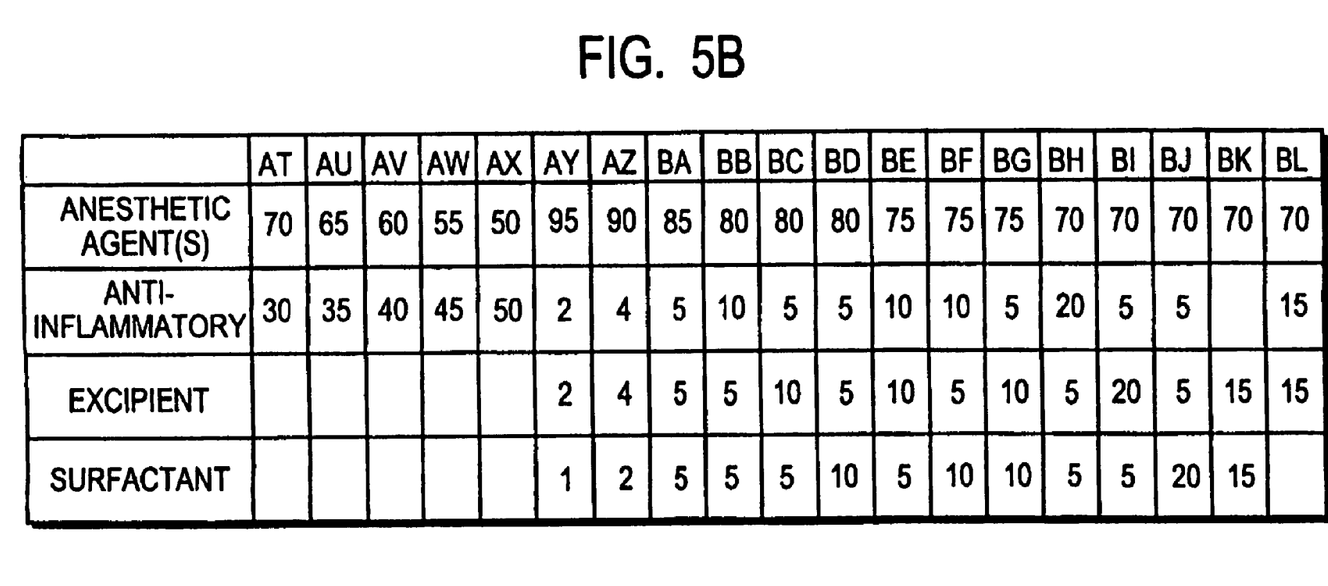
FIG. 5B recites Applicants' formulations AT through BL which include one or more anesthetic agents in combination with one or more additional ingredients.

In certain embodiments, Applicants' pain relief pellets comprise one or more anesthetic agents, including those used in caudal, epidural, inhalation, injectable, retrobulbar, and spinal applications, such as bupivacaine, lidocaine, prilocaine, and mixtures thereof. In these embodiments, the one or more anesthetic agents are present in an amount between about 5 weight percent and about 95 weight percent. FIGS. 5A and 5B recite Applicants' formulations AA through BL which include one or more anesthetic agents in combination with one or more additional ingredients discussed below.

Figure 6A:
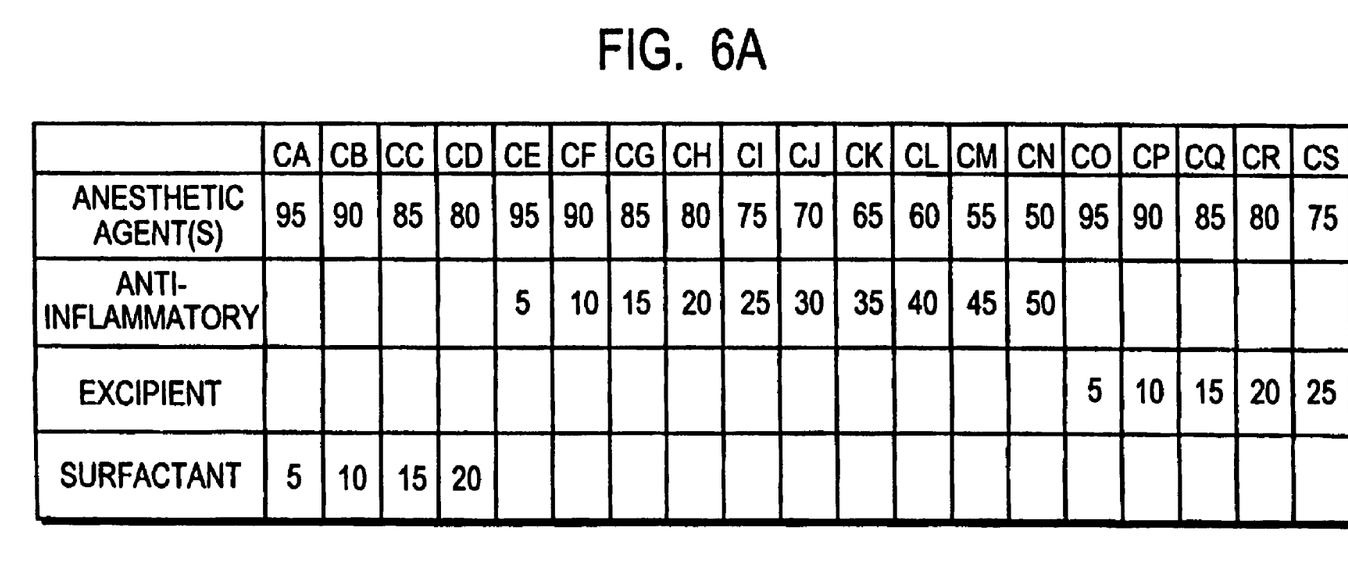
FIG. 6A recites Applicants' formulations CA through CS which include one or more analgesic agents in combination with one or more additional ingredients.
Figure 6B:
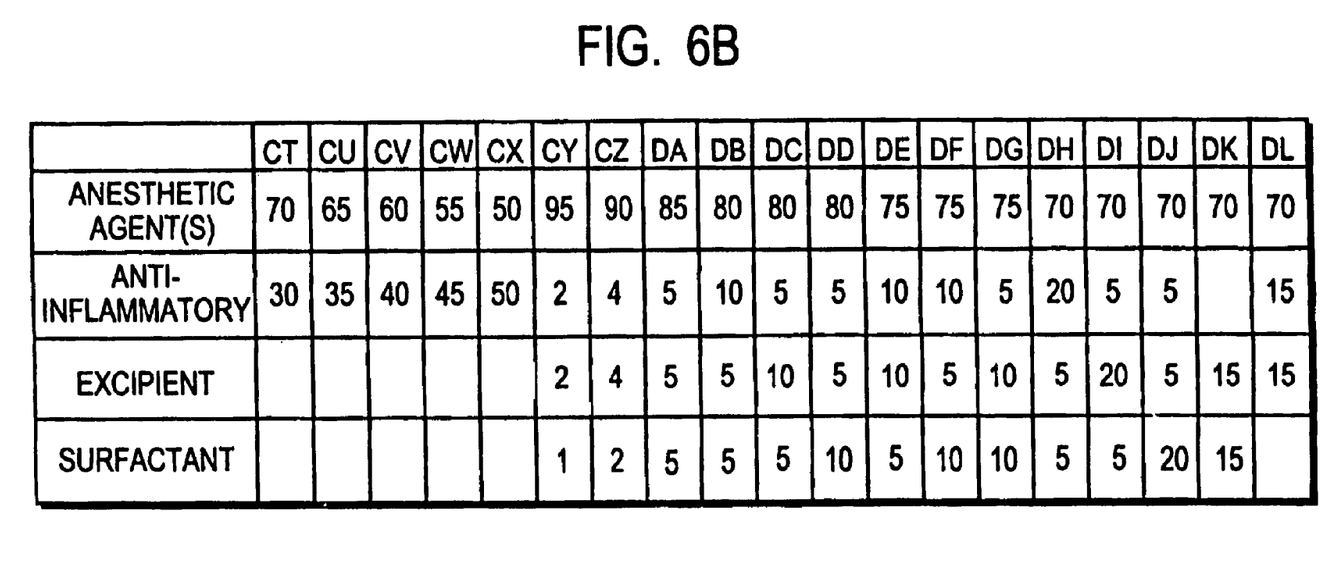
FIG. 6B recites Applicants' formulations CT through DL which include one or more analgesic agents in combination with one or more additional ingredients.

In alternative embodiments, Applicants' pain relief pellets comprise one or more analgesic agents, such as acetaminophen, ibuprofen, fluriprofen, ketoprofen, voltaren, phencetin, salicylamide, and mixtures thereof. In these embodiments, the one or more analgesic agents are present in an amount between about 5 weight percent and about 95 weight percent. FIGS. 6A and 6B recite Applicants' formulations CA through DL which include one or more analgesic agents in combination with one or more additional ingredients discussed below.

Figure 4:
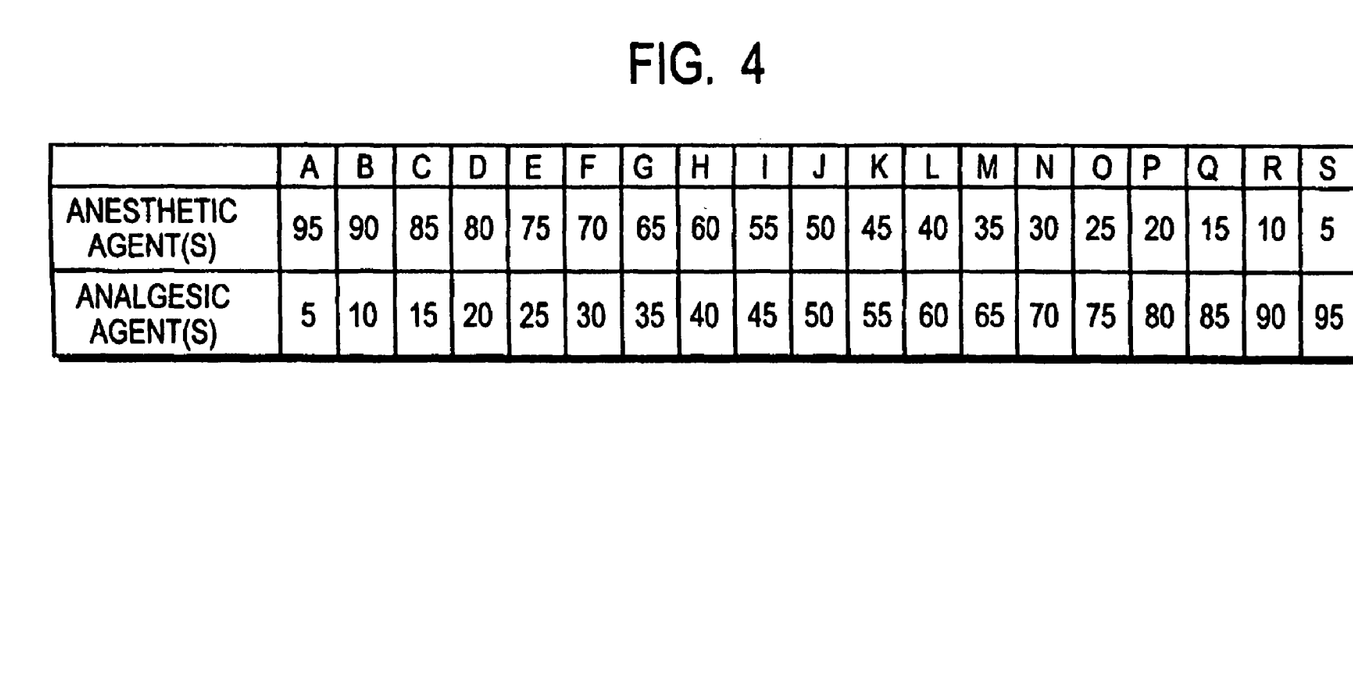
FIG. 4 recites Applicants' formulations A through S, wherein those formulations comprise one or more anesthetic agents in combination with one or more analgesic agents.

In yet other embodiments, Applicants' pain relief pellets comprise one or more anesthetic agents in combination with one or more analgesic agents. In these embodiments, the one or more anesthetic agents in combination with the one or more analgesic agents are present in an aggregate amount between about 5 weight percent and about 95 weight percent. FIG. 4 recites Applicants' formulations A through S, wherein those formulations comprise one or more anesthetic agents in combination with one or more analgesic agents.

Figure 7A:
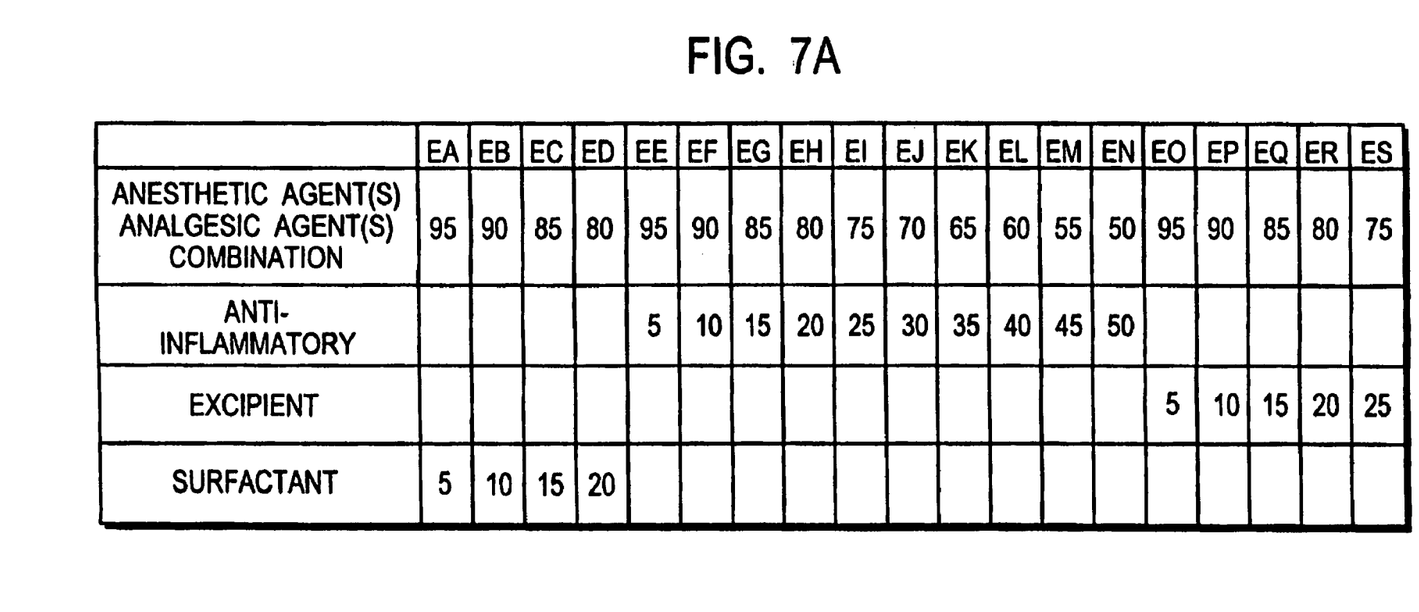
FIG. 7A recites Applicants' formulations EA through ES which include one or more anesthetic agents in combination with one or more analgesic agents in combination with one or more additional ingredients.
Figure 7B:
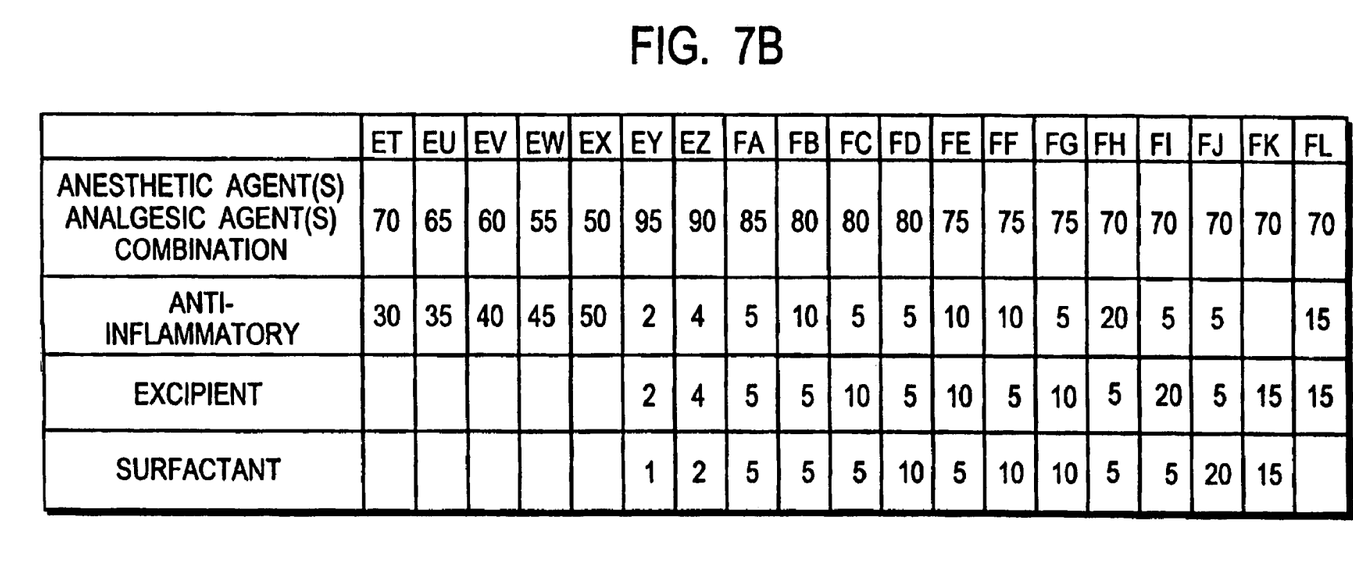
FIG. 7B recites Applicants' formulations ET through FL which include one or more anesthetic agents in combination with one or more analgesic agents in combination with one or more additional ingredients.

The weight percentages recited in FIG. 4 represent only the anesthetic/analgesic component of Applicants' pain relief formulation. In contrast, each formulation recited in FIGS. 7A and 7B includes one of the formulations recited in FIG. 4 in combination with one or more additional ingredients discussed below. For example, formulation EA (FIG. 7A) comprises an anesthetic agent(s)/analgesic agent(s) component present at about 95 weight percent in combination with a surfactant component present at about 5 weight percent. The anesthetic agent(s)/analgesic agent(s) component of formulation EA includes any of the formulations recited in FIG. 4. Thus, formulation EA includes at about a 95 weight percentage level, one or more of compositions AA through AS.

In certain embodiments, Applicants' implantable pellet also comprises one or more anti-inflammatory agents. By anti-inflammatory agent, Applicants mean a composition that minimizes injury-produced vascular dilatation and the greatly increased blood flow associated therewith, and/or exudation of fluid from blood vessels into tissues with concomitant swelling, and/or migration of leukocytes into the tissues, and/or gelation of fibrogen in intercellular spaces.

In certain embodiments, the one or more anti-inflammatory agents are selected from the group comprising, but not limited to, corticosteriods, keratolytics, and mixtures thereof. The one or more anti-inflammatory agent components of Applicants' composition are present in an amount up to about 90 weight percent.

Applicants' composition is formulated so as to be biodegradable in the target animals, including humans, and to control release of the active ingredients. In certain embodiments, Applicants' anesthetic composition includes one or more excipients, including but not limited to, polyethylene glycol, starch, dextran, polyvinylalcohol, poly 2-ethyl-2-oxazoline, and mixtures thereof. In certain embodiments, such excipients are present in an amount at up to about 50 weight percent. In other embodiments, such excipients are present in an amount between about 5 weight percent and about 25 weight percent. In alternative embodiments, such excipients are present in an amount between about 10 weight percent and about 20 weight percent.

Poly-2-ethyl-2-oxazoline is a water-soluble polymeric material. As those skilled in the art will appreciate, poly 2-ethyl-2-oxazoline comprises substituted polyethyleneimine II. Polymer II can be formed by a ring-opening polymerization of 2-ethyloxazoline I.

In certain embodiments, Applicants' implantable composition includes polymer II having a number average molecular weight of about 5,000, i.e. n equals about 50. This polymeric material is sold in commerce under the name AQUAZOL® 5 by Polymer Chemistry Innovations, Inc., 4231 South Fremont, Tucson, Ariz. 85714. In other embodiments, Applicants' implantable composition includes polymer II having a number average molecular weight of about 50,000, i.e. n equals about 500. This polymeric material is sold in commerce under the name AQUAZOL® 50 by Polymer Chemistry Innovations, Inc. In alternative embodiments, Applicants' implantable composition includes polymer II having a number average molecular weight of about 500,000, i.e. n equals about 5000. This polymeric material is sold in commerce under the name AQUAZOL® 500 by Polymer Chemistry Innovations, Inc.

In certain embodiments, Applicants' pain relief pellets comprise one or more surfactants. Such surfactants are selected from the group consisting of anionic surfactants, amphoteric surfactants, non-ionic surfactants, and mixtures thereof. Certain embodiments of Applicants' pain relief pellet include one or more nonionic surfactants having a Hydrophilic Lipophilic Balance ("HLB") between about 5 and about 20. Such nonionic surfactants include polyoxyethylene/polyoxypropylene block co-polymers, polyoxyethylene/alkyl ethers, polyoxyethylene sorbitan esters, and mixtures thereof. In certain embodiments, the surfactant component of Applicants' implantable composition is present in an amount up to about 20 weight percent. In other embodiments, such one or more surfactants are present in an amount between about 1 weight percent and about 10 weight percent. In alternative embodiments, such one or more surfactants are present in an amount between about 3 weight percent and about 5 weight percent.

The rate of in vivo release from an implanted pellet comprising one or more anesthetic agents, and/or one or more analgesic agents, and/or one or more anti-inflammatory agents, can be adjusted by: (i) varying the weight percentage of one or more water soluble polymeric excipients, such as poly 2-ethyl-2-oxazoline, and/or (ii) including a first surfactant and varying the weight percentage of that first surfactant, (iii) including a first surfactant at a first weight percentage level and a second surfactant at a second weight percentage level, and varying the ratio between said first weight percentage level and said second weight percentage level, and/or (iv) including one or more non-ionic surfactant(s) and varying the HLB(s) of those one or more non-ionic surfactants. Thus, the inclusion of a water-soluble, polymeric excipient in combination with one or more surfactant allows the formulator to adjust the rate of time release of the anaesthetic agents/analgesic agents/anti-inflammatory agents comprising Applicants' implantable pellets. In addition, the rate of systemic delivery of one or more pharmaceutical agents released from a pharmaceutical pellet implanted in an animal and disposed adjacent one or more of Applicants' implantable pellets can be adjusted by: (i) including a first surfactant and varying the weight percentage of that first surfactant, (ii) including a first surfactant at a first weight percentage level and a second surfactant at a second weight percentage level, and varying the ratio between said first weight percentage level and said second weight percentage level, and/or (iii) including one or more non-ionic surfactant(s) and varying the HLB(s) of those one or more non-ionic surfactants.

In certain embodiments, Applicants' pain relief pellet includes one or more lubricants, including, for example, magnesium stearate and/or croscarnellose sodium, especially as sold under the trademark Ac-Di-Sol® by FMC. Such lubricants are present in an amount up to about 5.0 weight percent. Applicants' anesthetic composition may optionally also include a wide range of additives to facilitate application, to control release, to stabilize the composition and for other reasons well known in the art.

In certain embodiments, Applicants' method utilizes an implanter having a pellet magazine in combination with an injection needle, as well as structure permitting injection of pellets from the magazine through the needle for implantation under the skin of an animal. In certain embodiments of Applicants' method, the magazine is loaded with pain relief pellets and pharmaceutical pellets for distribution in sequence singly. In alternative embodiments, the magazine is loaded with pain relief pellets and pharmaceutical pellets for distribution in multiples into the same injection site.

Broadly speaking, the pellet system used in Applicants' method includes an implanter apparatus for subcutaneously implanting pharmaceutical pellets in an animal through the bore of a hypodermic needle which is remotely coupled to a pellet magazine, and a plurality of pellets sized to be implanted through the needle and positioned in the magazine for selective alignment of a pellet with the needle. In one embodiment, the pellets include one or more pharmaceutical doses, and at least one pain relief pellet. In certain embodiments, that pain relief pellet includes one or more anti-inflammatory agents. These various pellets are arranged in the magazine in sequential order for simultaneous delivery of a pharmaceutical dose and an anesthetic/analgesic/anti-inflammatory dose as part of a single injection.

Figure 1:
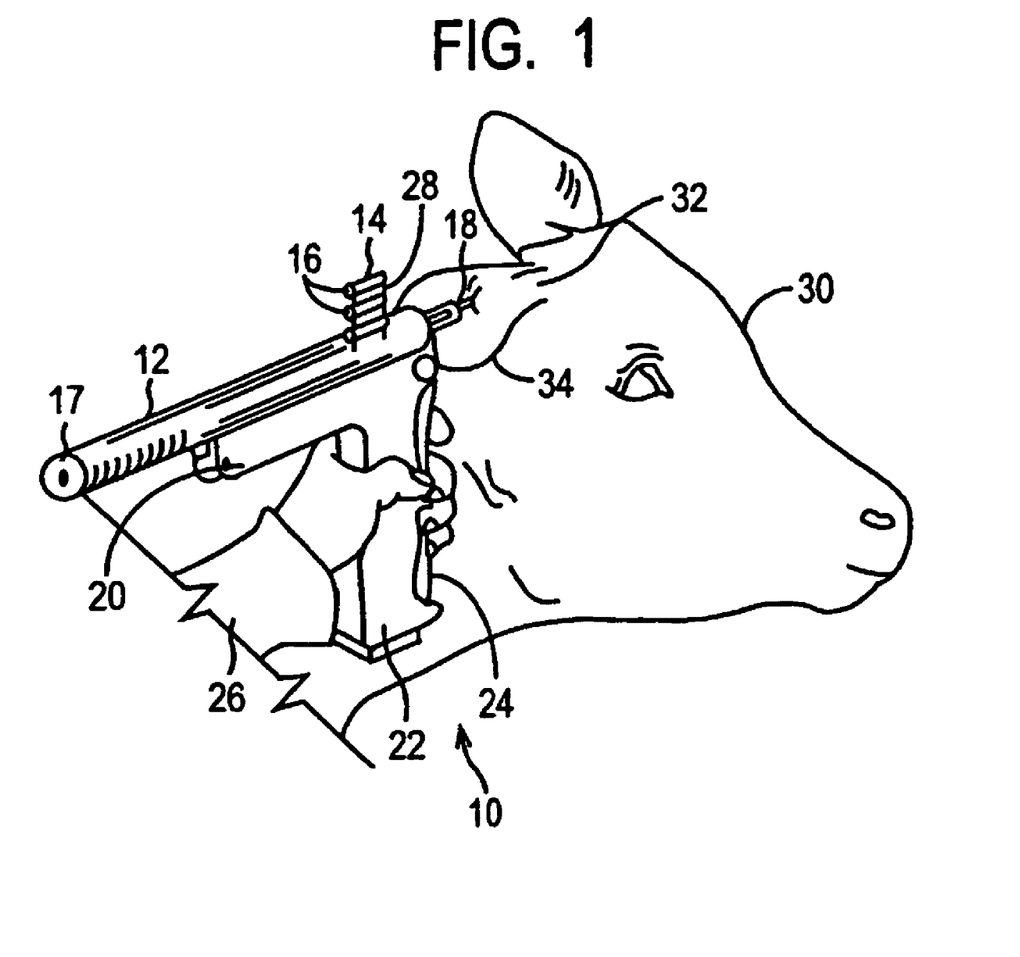
FIG. 1 is a fragmentary perspective view of an implantation apparatus of use when employing Applicants' method to relieve pain.

Referring to FIG. 1, general the reference numeral 10 represents a pellet implantation system in accordance with the invention. The implantation system 10 broadly includes a slide action implanter apparatus 12 which is used to implant solid form drugs or pharmaceuticals, such as pain relief pellets 40 (FIG. 2) and pharmaceutical pellets 42 (FIG. 2) from a magazine strip 16 into an animal 30 through a hypodermic needle 18. The needle 18 is utilized by an operator 26 to create an opening 44 that produces an implant receiving puncture 44 (FIG. 2) in the animal 30.

A suitable implanter apparatus 12 is illustrated and described in detail in U.S. Pat. No. 5,522,797, which is hereby incorporated herein, and generally includes a housing 20 having a grip 22 with a trigger assembly 24 pivotally mounted therein. An impeller 17 is slidably mounted within the housing 20 in alignment with an interior bore 46 (FIG. 2) of the needle 18 and aligned chambers 16 of the loaded pellet magazine strip 14. The needle 18 is used to puncture through the skin or hide 32 of an animal's ear 34, and the trigger 24 is squeezed toward the grip 22 of the housing 20 to initiate injection of the pellets 40 and 42 and so as to cause the impeller 17 to be urged through the magazine chamber 16 and needle bore 46, thereby forcing the pellets 40 and 42 through the bore 46 of needle 18 and into the puncture 44 in the ear 34.

Each magazine strip 14 of the implanter 12 typically contains multiple parallel aligned pellet doses stored in corresponding pellet chambers 16, which are connected by interconnecting webs 28. The chambers 16 are slightly conical in shape and are arranged in a side-by-side parallel relation. The chambers 16 may have internal frictional formations such as beads or posts (not shown) to retain the pellets 40 and 42 therein prior to insertion and which can be easily bypassed by application of pressure to the trigger 24. A plurality of strips 14 can be connected in end-to-end relation to increase the implanting capacity before the implanter 12 requires reloading. As the pellets 40 and 42 in an individual magazine strip 14 are exhausted the empty strip 14 can be detached from the remaining strips 14 located in the implanter 12 and discarded.

Each pellet chamber 16 is loaded with an arrangement of pellets 40 and 42. The pellets 40 and 42 are composed of one or more active ingredients, either alone, formed into a pellet, in conjunction with one or more excipients, formed as part of a polymeric based release system such as co-extruded polymers or matrix polymer systems, or included as part of a delivery system based on mass transfer through an opening or a gel matrix, either by diffusion or osmotic pressure pumping of the active ingredient.

Pellets 42 are formulated to include pharmaceuticals such as antibiotics, insulin, endocrine hormones (such as growth and birth control hormones), vaccines, parasiticides or other biocides. Thus in certain embodiments, one pellet 40 contains an anesthetic/analgesic composition/anti-inflammatory composition, and the other pellet 42 contains one or more pharmaceutical agents. It is foreseen that the number of pellets for each group may vary or that the pain relief agent(s) and other non-pain relief pharmaceuticals may be mixed in one or more of the pellets 40.

Each magazine chamber 16 is prefilled with a preferred number of discrete pellets 42, each containing a dose of one or more pharmaceuticals such as trenbolone acetate bovine growth hormone, along with at least one pellet 40 containing an anesthetic/analgesic/anti-inflammatory composition. The magazine strip 14 is preferably loaded onto implanter housing 20 in an orientation so that the pharmaceutical pellet 42 will be delivered first, followed by the anesthetic pellet 40.

Figure 2:
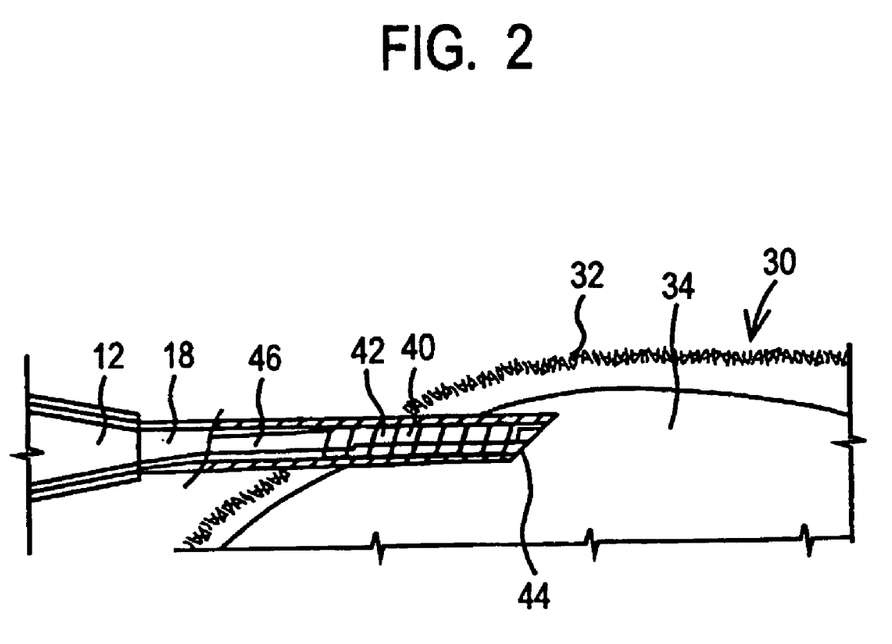
FIG. 2 is a fragmentary cross-sectional view showing Applicants' implantable pain relief pellets disposed within the implantation apparatus.
Figure 3:
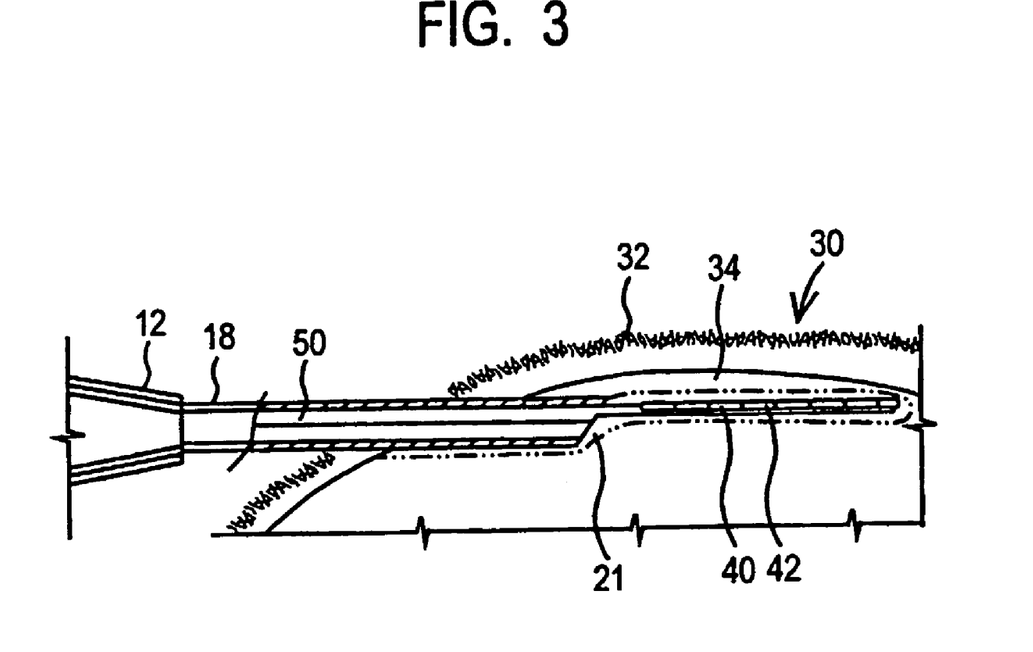
FIG. 3 is a fragmentary cross-sectional view showing implantation of Applicants' pain relief pellets.

In use, an operator grasps the implanter 12 by the grip 22 and urges the needle 18 into the hide 32 and under the skin of the target animal 30 to make the implant-receiving puncture 44. The puncture 44 shown in FIG. 2 is incomplete and the depth of the implant receiving puncture 44 shown in FIG. 2 is about half of the total depth as shown in FIG. 3. The operator 26 depresses the trigger member 24, thereby propelling a pin 50 (FIG. 3) of the impeller member 17 forwardly through an aligned magazine chamber 16, forcing the pellets 40 and 42 through the needle bore 46 and into the implant receiving puncture 44. The operator 26 then withdraws the needle 18, leaving the pellets 40 and 42 in the implant-receiving puncture 44.

While the pharmaceuticals in pellet 42 are absorbed and utilized systemically by the animal 30, in one embodiment pellet 40 preferably delivers most of its dose at the site of the implant receiving puncture 44, although some of the anesthetic/analgesic/anti-inflammatory agent(s) may be absorbed and carried systemically. In this embodiment, pellet 40 is preferably specifically formulated to deliver its dose locally rather than systemically, and at a controlled, predetermined rate over a preselected period of time. In another embodiment, pellet 40 is formulated to deliver a systemic anesthetic/analgesic/anti-inflammatory dose.

Those skilled in the art will appreciate that the magazine strip 14 may be loaded for selective injection of more than one pain relief pellet 40. Where a number of pellets 42 of pharmaceutical are to be delivered, the pharmaceutical may be sandwiched between two or more pain relief pellets to provide localized anesthetic release at both ends of a long implant receiving puncture 44. It is foreseen that in other embodiments pain relief pellets may be alternated in a stack of pellets of other pharmaceuticals, for delivery throughout the implant-receiving puncture 44.

Applicants' implantable pain relief pellets, and method to relieve pain using same, may be employed efficaciously with cows, horses, sheep, swine, dogs, cats or any other suitable animal, including humans.

While the invention has been described in detail herein in accordance with certain preferred embodiments thereof, many modifications and changes therein my be effected by those skilled in the art. Accordingly, it is intended by the appended claims to cover all such modifications and changes as fall within the true spirit and scope of the invention.

We claim:

1. An implantable pellet, comprising 95 weight percent of one or more pain relief agents, and 5 weight percent poly-2-ethyl-2-oxazoline having a formula:

wherein n is 5000.